US006585512B2

(12) United States Patent
Van Hale (10) Patent No.: US 6,585,512 B2
(45) Date of Patent: Jul. 1, 2003

(54) ASPIRATION UNIT

(76) Inventor: Gregory L. Van Hale, 247 W. Glenoaks Blvd., Glendale, CA (US) 91202

( * ) Notice: Subject to any disclaimer, the term of this patent is extended or adjusted under 35 U.S.C. 154(b) by 0 days.

(21) Appl. No.: 09/982,651

(22) Filed: Oct. 17, 2001

(65) Prior Publication Data

US 2003/0073054 A1 Apr. 17, 2003

(51) Int. Cl.[7] .............................................. A61C 17/06
(52) U.S. Cl. ....................................................... 433/91
(58) Field of Search ............................. 433/91, 92, 93, 433/94, 95, 96, 99

(56) References Cited

U.S. PATENT DOCUMENTS 4,061,146 A * 12/1977 Baehr et al. ................ 606/107
5,122,153 A * 6/1992 Harrel ........................ 606/180
5,531,722 A    7/1996 Van Hale

* cited by examiner

*Primary Examiner*—Kevin Shaver
*Assistant Examiner*—Melba Bumgarner
(74) *Attorney, Agent, or Firm*—J. E. Brunton

(57) ABSTRACT

A readily disposable aspiration unit that can be connected to various dental instruments of conventional design including ultrasonic scalers. The aspiration unit includes a novel suction means for automatically carrying away from the operative field cooling water and debris generated during the performance of the scaling procedure. The unit further includes a tip-encompassing shroud that uniquely functions as a suction scoop for automatically capturing aerosols in the operative field including aerosols containing saliva, blood, tissue, calculus and like adherent deposits, which are generated during the scaling procedure.

20 Claims, 5 Drawing Sheets

ASPIRATION UNIT

BACKGROUND OF THE INVENTION

1. Field of the Invention

The present invention relates generally to dental instruments. More particularly, the invention concerns an improved, disposable aspirating unit usable with f dental instruments of conventional construction for cutting, drilling, aspirating and scaling operations. The aspirating unit has at its distal end a vacuum scoop that circumscribes the scaler tip and expeditiously carries away particulate matter generated during operation of the scaler as well as controlling aerosols.

2. Discussion of the Invention

A number of different types of ultrasonic scalers have been suggested in the past. Typically such devices include a curved tip for supplying high frequency vibrations that effectively remove adherent deposits from the teeth and bits of inflamed tissue from the walls of the gingival crevice. Most of the prior ultrasonic scalers include an electrically operated hand piece and one or more autoclavable tips that can be removably connected to the hand piece. The tip of the scaler is generally interconnected with an electrically operated power unit, which provides high frequency vibration to the tip in the range of between about 5,000 Hertz and about 35,000 Hertz. Exemplary of such ultrasonic scalers are those offered for sale by Dentsply International, Inc. of York, Pa.; J. R. Rand Corporation of Deer Park, N.Y.; and Spartan U.S.A. of Fenton, Mo.

During operation of the conventional prior art ultrasonic scalers, substantial aerosol contamination results. More particularly, during the scaling procedure, the prior art devices typically generate a substantial aerosol spray of blood, saliva, tissue, calculus and other particulate matter, which can contaminate large areas of the operative field and adjacent areas.

Some prior art ultrasonic scalers are provided with a source of cooling water, which can be directed toward the work area. These devices tend to cause a buildup of water in the patient's mouth, which must be periodically removed using conventional suction devices. The cooling water also tends to substantially increase the production and spread of aerosols. Generally these devices include an elongated tube having a suction nozzle at one end, which is disposed within the patient's mouth proximate, the tooth being worked on. These suction devices are generally unwieldy and must be operated by the dental assistant as the dentist performs the scaling procedure. Accordingly, two people, that is the dentist and the dental assistant, are often required during the dental procedure.

Various attempts have been made in the past to overcome the drawbacks set forth in the preceding paragraphs by providing a disposable aspiration unit that can be removably interconnected with commercially available scalers of conventional design. One of the most successful of these units was developed by the present inventor and is described in U.S. Pat. No. 5,531,722 which was issued to the present inventor. Similarly, attempts have been made in the past to provide suction devices for use with ultrasonic scalers. However, these devices have not received wide acceptance in the field. One such prior art suction device, which has been advertised for use with ultrasonic scalers is a device offered for sale by Periogiene Company of Fort Collins, Co.

As will be better understood from the description which follows, the disposable aspiration unit of the present invention comprises a substantial improvement over the unit described in U.S. Pat. No. 5,531,772 and provides a more compact, easier to use unit that effectively contains and carries away aerosols containing blood, tissue and particulate matter generated during the scaling procedure.

SUMMARY OF THE INVENTION

It is an object of the present invention to provide an improved, readily disposable or reusable aspiration unit that can be readily connected to conventional dental instruments such as handpieces, drills, air abrasion units, lasers and to ultrasonic scalers. The aspiration unit uniquely includes a novel suction means for automatically carrying away from the work site cooling water and debris generated during the performance of the scaling procedure.

More particularly, it is an object of the invention to provide a compact, easy to use aspiration unit of the aforementioned character which includes a tip-encmompassing shroud that uniquely functions as a suction scoop for automatically capturing aerosols in the operative field including aerosols containing saliva, blood, tissue, calculus and like adherent deposits which are generated during the scaling procedure.

Another object of the invention is to provide an aspiration unit including a novel suction system that can be connected to a conventional scaler so that the assemblage can be operated by the dentist or dental hygienist using one hand without the aid of a dental assistant thereby decreasing the number of people exposed to any pathogens encountered during the scaling procedure.

Another object of the invention is to provide an aspiration unit of the class described that is compatible with standard sources of vacuum typically found in dental facilities.

Another object of the invention is to provide an apparatus as described which dramatically decreases the amount of airborne particles, aerosols and other contaminates which may be generated during the scaling procedure.

Another object of the invention is to provide an apparatus of the aforementioned character that significantly reduces the time required for patient rinsing. Another object of the invention is to provide an aerosol unit of the character described in the preceding paragraph, which is of simple design for ease of manufacture and one, which can be inexpensively produced, in large volume.

Still another object of the invention is to provide an aspiration unit having a lightweight, plastic body portion which is disposable or reusable and can be removably attached proximate one end to a source of vacuum and is provided proximate its other with a suction scoop of novel design. More particularly, one form of the suction scoop includes a plurality of downwardly extending, flexible bristles that enhance the vacuum proximate the tip and efficiently captures the cooling water and the debris generated during the scaling operation.

Another object of the invention is to provide finger operated valve means for controlling the degree of vacuum created within said interior space of said elongated outer body.

Another object of the invention is to provide finger operated valve means as described in the preceding paragraph in which the valve means comprises a valve element having an aperture formed therein, the valve element being movable between a first position wherein the aperture is in alignment with the flow passageway to a second position wherein said aperture is out of alignment with the passageway.

BRIEF DESCRIPTION OF THE INVENTION

DESCRIPTION OF THE INVENTION

Figures 1, 7, 8:
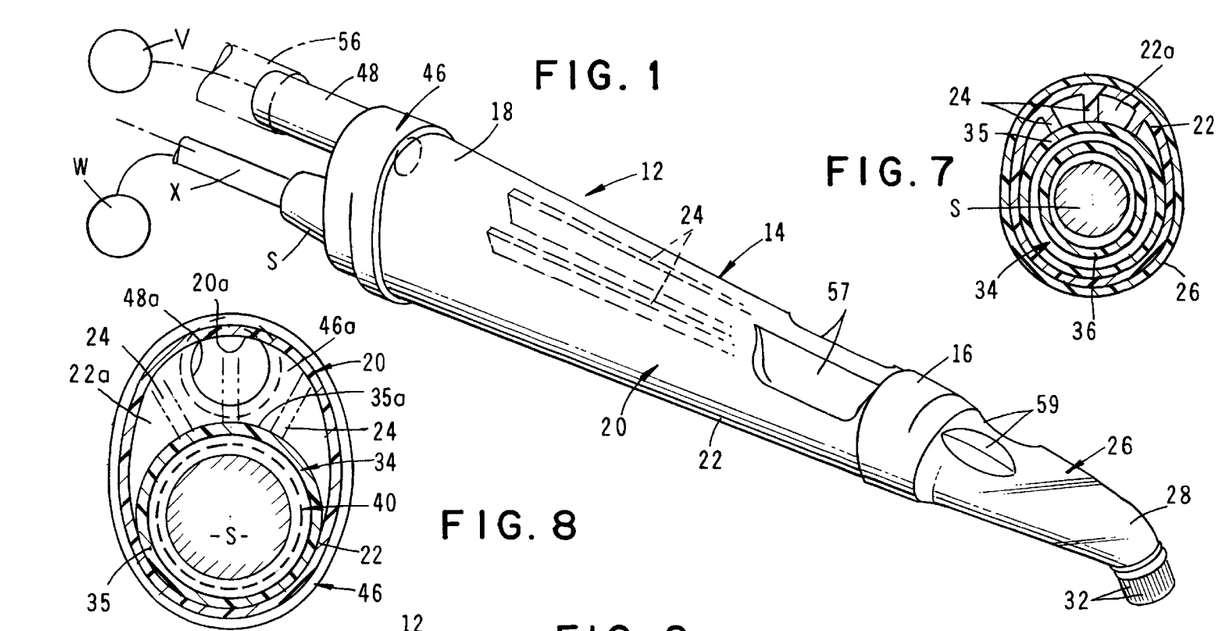
FIG. 1 is a generally perspective view of one form of aspiration unit of the invention showing the unit interconnected with the conventional scaler unit.
FIG. 7 is a cross-sectional view taken along lines 7—7 of FIG. 5.
FIG. 8 is a cross-sectional view taken along lines 8—8 of FIG. 5.
Figure 2:
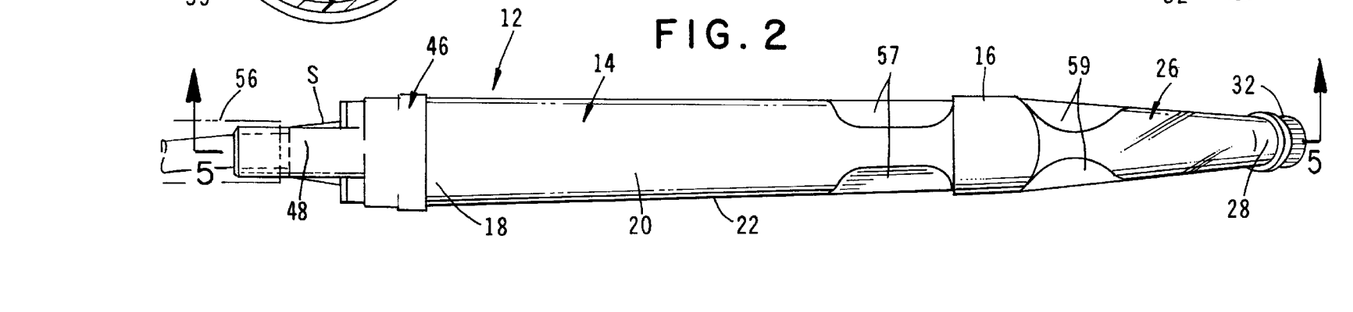
FIG. 2 is a top plan view of the assemblage shown in FIG. 1.

Referring to the drawings and particularly to FIGS. 1 and 2, one form of the aspiration unit of the present invention is there shown operably interconnected with a dental instrument such as a scaler "S" of a conventional design. The assembled unit, which is generally designated by the numeral 12, comprises an elongated, specifically configured, hand held assemblage 14 having first distal and second proximal end portions 16 and 18 respectively. As is best seen by referring to FIGS. 4 and 5, assemblage 14 includes an elongated, tapered outer body 20 having a circumscribing wall 22. Attached to and extending radially inwardly from wall 22 are three spaced apart standoffs 24, the purpose of which will presently be described.

Figures 3, 4:
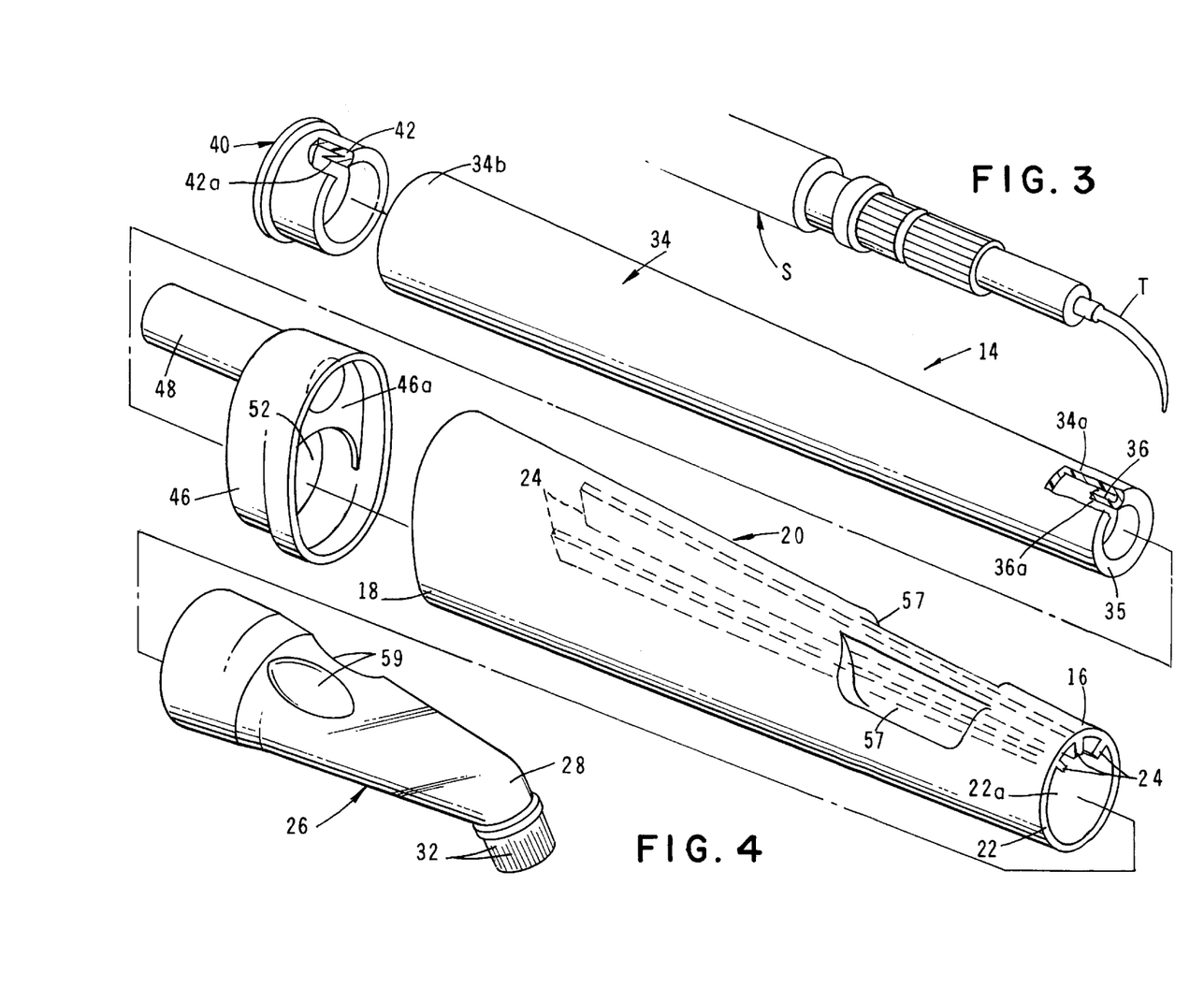
FIG. 3 is a generally perspective view of the forward portion of a scaler of conventional construction of the character with which the aspiration unit of the invention can be used.
FIG. 4 is a generally perspective, exploded view of the aspiration unit.
Figures 5, 6:
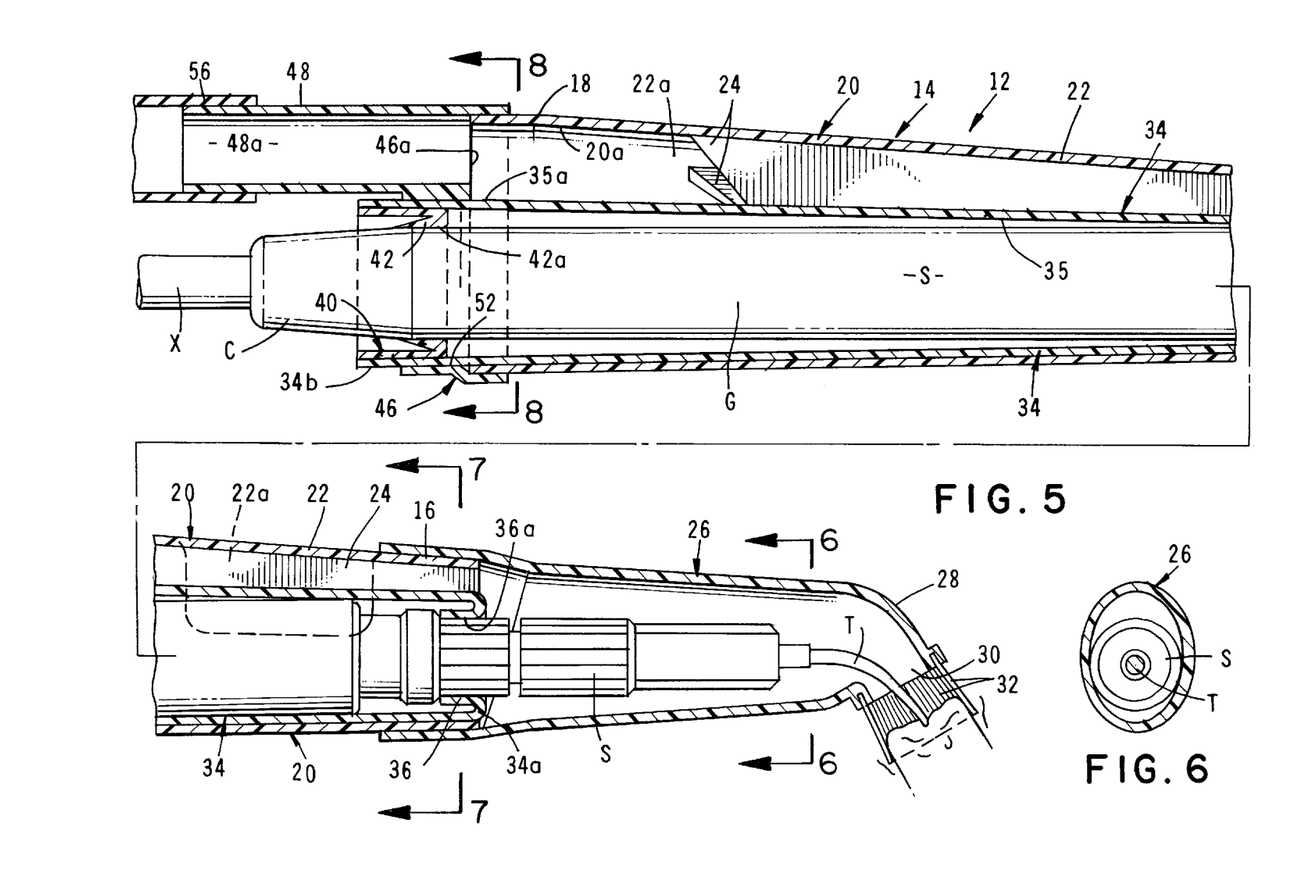
FIG. 5 is an enlarged, cross-sectional view taken along lines 5—5 of FIG. 2.
FIG. 6 is a cross-sectional view taken along lines 6—6 of FIG. 5.

Wall 22 progressively increases in diameter from the first end portion 16 to the second end portion 18 so as to define a longitudinally extending interior space 22a (FIGS. 4 and 5). Provided proximate the first or distal end portion 16 of body 20 is an intake means shown here as a specially configured, partially transparent shroud 26, having a scoop-like portion 28 that includes an open mouth 30 (FIG. 5). Being at least partially transparent, shroud 26 in no way obstructs the vision of the tip during the scaling procedure.

An important feature of the present invention is the provision of a multiplicity of downwardly extending, flexible bristles 32 that are attached to the mouth portion 30 of scoop-like portion 28 and are arranged to circumscribe mouth 30 in the manner best seen in FIG. 5. Bristles 32 act both as a collector for collecting debris and as a suction enhancer for enhancing the suction proximate the operative field. In using the device, the flexible bristles function to conveniently circumscribe the outer surface of the tooth that is subject of the scaling procedure. Preferably bristles 32 are constructed of a flexible plastic filament such as a nylon filament and are preferably between about 0.003 and about 0.0006 inches in diameter.

Telescopically received within interior space 22a is an elongated, tapered inner body 34 having a circumscribing wall 35 that is generally circular in cross-sectional at any point. Inner body 34 terminates at its first or forward end 34a in an inturned flange 36 having a longitudinally extending surface 36a that frictionally engages the forward portion of the scaling instrument in the manner best seen in FIG. 5. Flange 36 here comprises the inner body gripping means for gripping the dental instrument. Affixed at the opposite or second end of inner body 34 is a gripping collar 40 that also includes an inturned flange 42. Like flange 36, flange 42 includes a longitudinally extending gripping surface 42a that is adapted to frictionally engage the rearward portion of the scaling instrument in the manner shown in FIG. 5. Flange 42 here comprises a part of the gripping means of the invention for gripping the dental instrument. With the construction thus described, when the scaling instrument is telescopically inserted into the inner body 34, flanges 36 and 42 function to center and securely hold the scaling instrument in position within the inner body.

Referring particularly to FIGS. 3 and 5, it can be seen that hand held assemblage 14 includes a closure cap assembly 46 is affixed to the proximal end 18 of outer body 20. Assembly 46 includes an end wall 46a and a rearwardly extending connector means or tubular member 48 that is affixed to and extends from end wall 46a. Member 48 has an interior passageway or space 48a that communicates with interior space 22a of outer body 20. As best seen in FIG. 5, inner space 22a is defined between the inner surface of wall 22 of body 20 and the outer surface of wall 35 of inner body 34. As best seen in FIG. 4, end wall 46a of cap assembly 46 includes a lower portion that is provided with an opening 52 that is constructed and arranged to closely receive the rearward end of inner body 34, that is the end within which collar 40 is telescopically received (see FIG. 5). Body 20, body 34, shroud 26, collar 40 and cap assembly 46 are preferably all constructed from a moldable plastic.

It is to be noted that when cap assembly 46 is connected to outer body 20 with end 34b of inner body 34 positioned within opening 52, inner body 34 is securely held within the outer body 20. In this secured position, a substantial portion of wall 35 of body 34 is in engagement with and is supported by the previously identified standoffs 24. In similar fashion, the scaling instrument is centered and held securely in position within inner body 34 by inturned flanges 36 and 42. With the apparatus assembled in the manner shown in FIG. 5, a suitable source of vacuum can be interconnected with the connector means or tubular member 48 through the use of an elastomeric tube or conduit 56 that can be sealably interconnected with tubular member 48. The vacuum source "V" (FIG. 1) can comprise any suitable type of vacuum pump of standard construction. In operation the vacuum source creates a substantial vacuum within interior space 22a that is sufficient to capture and channel through mouth 30 and space 22a both the accumulated cooling water and the particulate contamination located proximate scaler tip "T". It is to be understood that sources of vacuum other than vacuum pumps can be used. These include in-office high and low-pressure sources of vacuum. For example, through proper design of cap assembly 46, low-pressure saliva ejection systems of the character typically found in dental offices can be used as the vacuum source.

As previously mentioned, scalers of the type shown in FIG. 3 are commercially available from a number of different sources and typically include a hand grip portion "G", which terminates at one end in a connector portion "C" that enables the scaler to be connected to the power unit and to a conventional source of cooling water "W" via a conduit "X" (FIG. 1). Conduit "X" provides both power and cooling water to the sealing tip "T".

With the ultrasonic scaler "S" securely positioned within assemblage 14 and with the vacuum source energized, the unit can be conveniently gripped by the dentist using the conveniently located finger gripping cavities 57 and 59 formed in the outer body and in the shroud 26 respectively. As indicated in FIG. 5, the portion of interior space 22a located between the inner surface 20a of wall 20 and the outer surface 35a of inner body 34 is such as to provide a passageway of substantial volume. As shown in the lower portion of FIG. 5, this passageway is in communication with mouth portion 30 of shroud 26 so that, when a vacuum is formed within interior space 22a by the vacuum pump, air will be drawn rapidly into mouth 30 of the shroud. The air will then pass around and about standoffs 24 and will flow smoothly through the passageway toward passageway 48a of connector 48. This inward flow of air into mouth 30 and through internal space 22a will efficiently draw into the interior space cooling water as well as particulate contamination generated by the tip "T" during the operation of the scaler device.

After the scaling procedure has been completed, conduit 56 can be easily disconnected from connector 48 and cap 46 can be readily separated from outside body 20. Once cap 46 has been removed, the scaler "S" can be pulled rearwardly from inner body 34 and transferred to the autoclave area for sterilization. This done, cap 46, collar 40, inner and outer bodies 34 and 20 and shroud 26, can be conveniently disposed of in an appropriate safe receptacle along with other contaminated waste generated in the dental office. Alternatively, the components can be sterilized or decontaminated for reuse.

Prior to the commencement of the next scaling procedure, a sterilized scaler unit can be conveniently inserted into a new assemblage made up of outer body 20, inner body 34 and gripping collar 40. This done, a new cap assembly 46 and a new shroud assembly 26 can be interconnected with outer body 20 in the manner shown in FIG. 5. This done conduit 56 can be connected to connector tube 48 making the unit ready for use by the dentist.

Figures 9, 11:
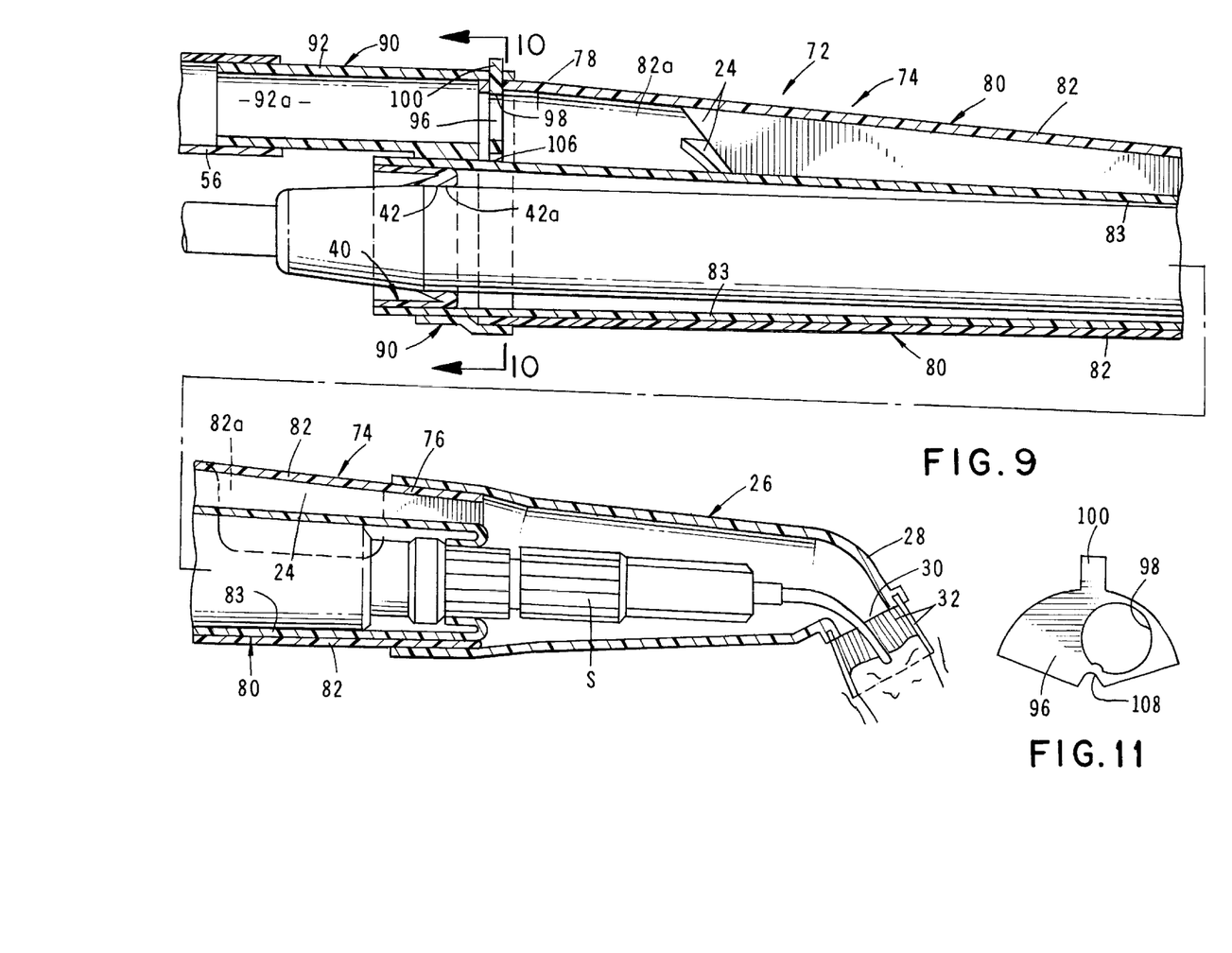
FIG. 9 is an enlarged cross-sectional view, similar to FIG. 5, but showing an alternate form of the apparatus of the invention that includes valve means for controlling the degree of vacuum being created at the shroud of the apparatus.
FIG. 11 is an enlarged front view of one form of the valve means of the invention.
Figure 10:
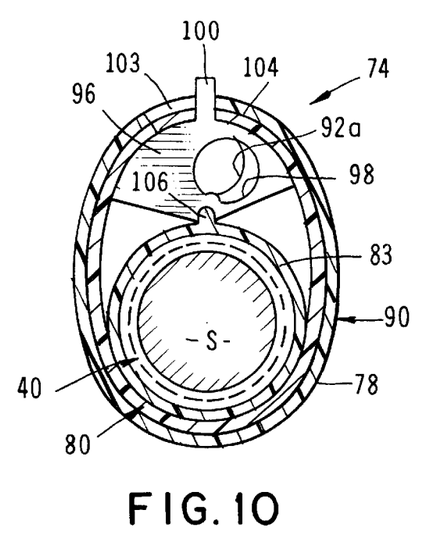
FIG. 10 is a cross-sectional view taken along lines 10—10 of FIG. 9.
Figure 12:
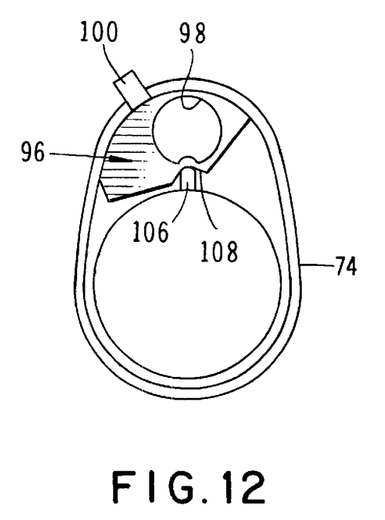
FIG. 12 is an enlarged view of the valve means of FIG. 11 mounted within the apparatus and showing the valve in a fully open position.

Referring next to FIGS. 9, 10 and 11, an alternate form of the aspiration unit of the invention is there shown operably interconnected with a scaler of a conventional design. This unit, which is generally designated by the numeral 72, is similar in many respects to that shown in FIGS. 1 through 8 and like numerals are used in FIGS. 9 through 14 to identify like components. Unit 72 comprises a hand held assemblage 74 having first and second end portions 76 and 78 respectively. As before, assemblage 74 includes a tapered outer body 80 having a wall 82 which is generally circular in cross-sectional at any point. Attached to and extending radially inwardly from wall 82 is a plurality of standoffs 24 that function in the manner previously described to support inner body 83. Wall 82 progressively increases in diameter from the first end portion 76 to the second end portion 78 so as to define a longitudinally extending interior space 82a. Provided proximate the first or distal end portion 76 of body 80 is an intake means that is of the construction previously described.

Affixed at the rearward end of outer body 80 and inner body 83 is a hollow cap 90 that is of similar construction to cap 46, but here, along with outer body 80, carries the novel valve means of the invention the character of which will presently be described. As before, when the scaling instrument is telescopically inserted into the inner body 34, cap 90 functions to center and securely hold the scaling instrument in position within the inner body.

Cap 90 includes a rearwardly extending tubular member 92 that defines an interior flow passageway 92a that communicates with interior space 82a. Cap assembly 90 also includes a lower portion that is provided with an aperture that is constructed an arranged to closely receive the rear end of inner body 83 and the hollow cap 40 that is telescopically received therewithin (see FIG. 5). When the inner body 83 is correctly positioned within outer body 80 and when the scaling instrument is correctly positioned within inner body 83, the apparatus can be interconnected with a suitable vacuum means by a conduit 56 that can be sealably interconnected with tubular member 92. The vacuum means can comprise any suitable type of vacuum pump of standard construction (not shown). In operation the vacuum pump creates a substantial vacuum within interior space 82a that is sufficient to capture and channel through space 82a both the accumulated cooling water and the particulate contamination located proximate scaler tip "T".

Figure 13:
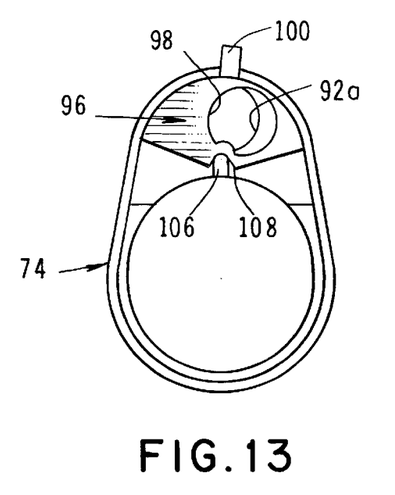
FIG. 13 is a view similar to FIG. 12, but showing the valve in a partially closed position.
Figure 14:
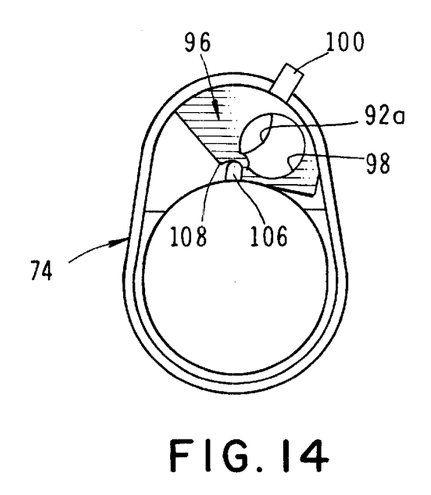
FIG. 14 is view similar to FIG. 13, but showing the valve moved to a more closed position.

Referring particularly to FIGS. 9, 10 and 11, one form of the novel valve means of the invention is there shown. As best seen in FIGS. 9 and 10, the valve means is housed within the hand held assemblage 74 at a location proximate tubular member 92. In the present form the invention the valve means comprises a generally fan shaped, planar valve element 96 that has an aperture 98 formed therein (FIG. 11). Valve element 96 is pivotally movable within hand held assemblage 74 between a first position shown in FIG. 12 where aperture 98 is aligned with flow passageway 92a defined by tubular member 92 and a second position shown in FIG. 14 where the aperture is out of alignment with passageway 92. As indicated in FIG. 13, valve element 98 can also be moved to intermediate positions between the position shown in FIG. 12 and the position shown in FIG. 14 so as to closely control the degree of vacuum created within interior space 82a at the shroud any given point in time.

As shown in FIG. 11, valve element 96 also includes a finger engaging protuberance 100 that extends outwardly through slots 103 and 104 formed in body portion 74 and closure cap 90. With this construction, protuberance 100 can be engaged by the finger of the user to move the valve element into various positions, as by way of example, those illustrated in FIGS. 12, 13 and 14. To enable the desired pivotal movement of the valve element within the apparatus, body portion 83 is provided with a fulcrum 100 that is adapted to be received within a notch 108 formed in the lower portion of valve element 96 (FIG. 11).

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An aspiration unit for use with a dental instrument having a hand grip portion and a tooth-engaging portion, said aspiration unit comprising:
   (a) an elongated outer body having a distal end, a proximal end and a wall defining an elongated interior space;
   (b) an elongated inner body mounted within said elongated outer body, said elongated inner body having a first end and a second end and a wall defining an interior space, said dental instrument being receivable within said interior space of said elongated inner body;
   (c) an end cap assembly removably connected to said proximal end of said outer body, said end cap assembly including:
      (i) an end wall; and
      (ii) a connector means connected to said end wall for connecting the unit with a source of vacuum, said connector means having a flow passageway in communication with said interior space of said elongated outer body;
   (d) intake means connected to said distal end of said outer body for channeling particulate matter into said interior space of said outer body, said intake means comprising a mouth portion in communication with said interior space of said elongated outer body; and
   (e) vacuum means connected to said connector means for creating a vacuum within said interior space of said elongated outer body.

2. The aspiration unit as defined in claim 1 in which said mouth portion of said intake means comprises a multiplicity of bristles circumscribing the tooth-engaging portion of the dental instrument.

3. The aspiration unit as defined in claim 1 in which said elongated outer body further includes a radially inwardly extending standoff connected to said wall of said outer body for engagement with said inner body.

4. The aspiration unit as defined in claim 1 in which said intake means is adapted to capture particulate matter located proximate the tooth-engaging portion of the dental instrument.

5. The aspiration unit as defined in claim 1 in which said elongated inner body further includes gripping means for gripping the dental instrument.

6. The aspiration unit as defined in claim 5 in which said gripping means comprises an inturned flange provided on said wall of said elongated inner body proximate said first end thereof.

7. The aspiration unit as defined in claim 6 further including a gripping collar connected to said second end of said elongated inner body for gripping the dental instrument.

8. The aspiration unit as defined in claim 7 in which said gripping collar includes an inturned flange for gripping the dental instrument.

9. The aspiration unit as defined in claim 8 in which said gripping collar is telescopically received within said second end of said elongated inner body.

10. An aspiration unit for use with a dental instrument having a hand grip portion and a tooth-engaging portion, said aspiration unit comprising:
    (a) an elongated outer body having a longitudinal axis, a distal end, a proximal end and a wall defining an elongated interior space;
    (b) an elongated inner body mounted within said elongated outer body, said elongated inner body having a first end and a second end and a wall defining an interior space, said dental instrument being receivable within said interior space of said elongated inner body, said elongated inner body further comprising gripping means for gripping the dental instrument, said gripping means comprising an inturned flange provided on said wall of said elongated inner body proximate said first end thereof;
    (c) a gripping collar connected to said second end of said elongated inner body for gripping the dental instrument, said gripping collar including an inturned flange for gripping the dental instrument;
    (d) an end cap assembly removably connected to said proximal end of said outer body, said end cap assembly including:
       (i) an end wall having an opening for receiving said second end of said elongated inner body; and
       (ii) a connector means connected to and extending from said end wall for connecting said end wall with a source of vacuum, said connector means comprising a tube having a longitudinal axis extending substantially parallel to said longitudinal axis of said elongated outer body and including a flow passageway in communication with said interior space of said elongated outer body;
    (e) intake means connected to said distal end of said outer body for channeling particulate matter into said interior space of said outer body, said intake means comprising a mouth portion in communication with said interior space of said elongated outer body; and
    (f) vacuum means connected to said connector means for creating a vacuum within said interior space of said elongated outer body.

11. The aspiration unit as defined in claim 10 in which said mouth portion of said intake means comprises a multiplicity of flexible bristles circumscribing the tooth-engaging portion of the dental instrument.

12. The aspiration unit as defined in claim 10 in which said elongated outer body further includes a plurality of circumferentially spaced, radially inwardly extending standoffs connected to said wall of said outer body for engagement with said inner body.

13. The aspiration unit as defined in claim 10 in which said gripping collar is telescopically received within said second end of said elongated inner body.

14. An aspiration unit for use with a dental instrument having a hand grip portion and a tooth-engaging portion, said aspiration unit comprising:
    (a) an elongated, plastic outer body having a longitudinal axis, a distal end, a proximal end, a circumscribing wall defining an elongated interior space and a plurality of standoffs extending radially inwardly from said wall;
    (b) an elongated, plastic inner body mounted within said elongated outer body, said elongated inner body having a first end and a second end and a circumscribing wall defining an interior space, said dental instrument being receivable within said interior space of said elongated inner body, said elongated inner body further comprising gripping means for gripping the dental instrument, said gripping means comprising an inturned flange provided on said wall of said elongated inner body proximate said first end thereof;
    (c) a plastic gripping collar telescopically within said second end of said elongated inner body for gripping the dental instrument, said gripping collar including an inturned flange for gripping the dental instrument;
    (d) a plastic end cap assembly removably connected to said proximal end of said outer body, said end cap assembly including:

(i) an end wall having an opening for receiving said second end of said elongated inner body; and (ii) a connector means connected to and extending from said end wall for connecting said end wall with a source of vacuum, said connector means comprising a tube having a longitudinal axis extending substantially parallel to said longitudinal axis of said elongated outer body and including a flow passageway in communication with said interior space of said elongated outer body;

(e) intake means connected to said distal end of said outer body for channeling particulate matter into said interior space of said outer body, said intake means comprising:

(i) a mouth portion in communication with said interior space of said elongated outer body; and (ii) a multiplicity of flexible bristles connected to and extending from said mouth; and (f) vacuum means connected to said connector means for creating a vacuum within said interior space of said elongated outer body.

15. The aspiration unit as defined in claim 14 in which each of said multiplicity of flexible bristles comprise a filament having a diameter of between about 0.003 and about 0.0006 inches.

16. The aspiration unit as defined in claim 14 in which the said unit further includes cooling water means for cooling an area proximate the tooth-engaging portion of the instrument and in which said intake means is adapted to capture both cooling water and particulate matter located proximate the tooth-engaging portion of the dental instrument.

17. An aspiration unit for use with a dental instrument having a hand grip portion and a tooth-engaging portion, said aspiration unit comprising:

(a) a hand held assemblage including an elongated outer body having a distal end, a proximal end and a wall defining an elongated interior space;

(b) an elongated inner body mounted within said elongated outer body, said elongated inner body having a first end and a second end and a wall defining an interior space, said dental instrument being receivable within said interior space of said elongated inner body;

(c) a connector means connected to said outer body for connecting said interior space with a source of vacuum, said connector means having a flow passageway in communication with said interior space of said elongated outer body;

(d) intake means connected to said distal end of said outer body for channeling particulate matter into said interior space of said outer body, said intake means comprising a mouth portion in communication with said interior space of said elongated outer body;

(e) vacuum means connected to said connector means for creating a vacuum within said interior space of said elongated outer body; and (f) valve means carried by said hand held assemblage for controlling the degree of vacuum created within said interior space of said elongated outer body.

18. The apparatus as defined in claim 17 in which said valve means comprises a valve element having an aperture formed therein, said valve element being movable within said hand held assemblage between a first position wherein said aperture is in alignment with said flow passageway to a second position wherein said aperture is out of alignment with said passageway.

19. The apparatus as defined in claim 18 in which said valve element includes a finger engaging protuberance extending from said outer body for moving said valve element between said first and second positions.

20. The apparatus as defined in claim 19 in which said inner body includes a fulcrum and in which said valve element includes a notch for receiving said fulcrum.

* * * * *